US012383002B2

(12) United States Patent
Orrington, II et al.

(10) Patent No.: US 12,383,002 B2
(45) Date of Patent: Aug. 12, 2025

(54) PROTECTIVE APPARATUSES FOR MINIMIZING RISK OF TRANSMISSION OF INFECTION AND ASSOCIATED SYSTEMS AND METHODS

(71) Applicant: James L. Orrington, II D.D.S., P.C., Chicago, IL (US)

(72) Inventors: James L. Orrington, II, Flossmoor, IL (US); Michael Prince, Chicago, IL (US); Hyunchul Kim, Chicago, IL (US); McKayla Barber, Madison, WI (US)

( * ) Notice: Subject to any disclaimer, the term of this patent is extended or adjusted under 35 U.S.C. 154(b) by 610 days.

(21) Appl. No.: 17/091,012

(22) Filed: Nov. 6, 2020

(65) Prior Publication Data

US 2022/0142269 A1    May 12, 2022

(51) Int. Cl.
*A41D 13/11* (2006.01)

(52) U.S. Cl.
CPC ...... *A41D 13/1107* (2013.01); *A41D 2600/00* (2013.01)

(58) Field of Classification Search
CPC ...... A41D 13/11–1107; A41D 13/1184; A41D 2600/00; B08B 15/00–04; A61C 19/007;
(Continued)

(56) References Cited

U.S. PATENT DOCUMENTS

| 2,485,325 A | 10/1949 | Sloane |
| 2,726,054 A | 12/1955 | Lesley et al. |

(Continued)

FOREIGN PATENT DOCUMENTS

| CA | 2140718 A | 7/1996 |
| CN | 204788058 U | 11/2015 |

(Continued)

OTHER PUBLICATIONS

International Search Report for PCT Application No. PCT/US21/026531, dated Jul. 22, 2021; and associated written opinion.

(Continued)

*Primary Examiner* — Rachel T Sippel
(74) *Attorney, Agent, or Firm* — Chiacchio IP, LLC; Theodore J. Chiacchio

(57) ABSTRACT

Disclosed herein are protective apparatuses for minimizing the risk of transmission of SARS-CoV-2 and other infectious diseases between individuals in close proximity to one another. Said apparatuses may comprise a receiving component comprising a first aperture comprising a series of flanges; as well as a substantially transparent shield component. Protective apparatuses of the present disclosure may be used to protect dentists and other healthcare workers from transmission of infectious agents through aerosols and through transmission of droplets and other bodily fluids that may contain infectious agents and likewise may be used to protect patients in the same manner. Also disclosed herein are systems comprising such protective apparatuses installed to a substantially cylindrical suctioning device such as a vacuum hose or operatively attached to an articulating mechanical arm. Also disclosed herein are methods of using such protective apparatuses and systems to mitigate the risk of transmission of infectious diseases between, without limitation, patients and healthcare workers treating such patients.

17 Claims, 3 Drawing Sheets

(58) Field of Classification Search
CPC ....... A61M 16/00–0003; A61M 16/0087–009;
A61M 16/06–0655; A61M 2016/0661
See application file for complete search history.

(56) References Cited

U.S. PATENT DOCUMENTS

| | | | |
|---|---|---|---|
| 3,377,082 A | 4/1968 | Harvey | |
| 3,877,691 A | 4/1975 | Foster | |
| 4,444,183 A | 4/1984 | Heckendorn | |
| 4,559,939 A | 12/1985 | Levine et al. | |
| 4,781,108 A | 11/1988 | Nillson | |
| 4,832,042 A | 5/1989 | Poppendiek et al. | |
| 4,936,318 A | 6/1990 | Schoolman | |
| 4,949,714 A | 8/1990 | Orr | |
| 5,012,852 A | 5/1991 | Blackhurst | |
| 5,316,541 A | 5/1994 | Fischer | |
| D354,560 S | 1/1995 | Chase | |
| 5,497,295 A | 3/1996 | Gehly | |
| 5,620,407 A | 4/1997 | Chang | |
| 5,636,627 A * | 6/1997 | Rochester | A61M 16/009 |
| | | | 128/205.27 |
| 5,865,182 A | 2/1999 | Chen | |
| 6,309,222 B1 | 10/2001 | Billingsley | |
| 6,321,764 B1 | 11/2001 | Gauger et al. | |
| 6,322,754 B1 | 11/2001 | Buchmann et al. | |
| 6,338,675 B2 | 1/2002 | Winkelman | |
| 6,367,943 B1 | 4/2002 | Tocci et al. | |
| 6,471,579 B1 | 10/2002 | Blackshear | |
| 6,899,668 B2 | 5/2005 | Paranjpe | |
| 7,094,266 B2 | 8/2006 | Montgomery | |
| 7,503,890 B2 | 3/2009 | Kubicsko et al. | |
| 8,087,341 B2 | 1/2012 | Adler | |
| 8,234,822 B2 | 8/2012 | Proctor et al. | |
| 8,245,713 B2 | 8/2012 | Paschal, Jr. et al. | |
| 8,397,725 B2 | 3/2013 | Slaker et al. | |
| 8,568,501 B2 | 10/2013 | Kelso | |
| D704,934 S | 5/2014 | Blinka et al. | |
| D784,541 S | 4/2017 | Hilbig et al. | |
| 9,981,351 B2 | 5/2018 | Vanier | |
| 10,016,251 B2 | 7/2018 | Holman et al. | |
| 10,016,252 B1 | 7/2018 | Wren | |
| 10,182,754 B2 * | 1/2019 | Mendels | A61B 5/150992 |
| 10,420,386 B1 | 9/2019 | Jefferis et al. | |
| 10,596,282 B2 | 3/2020 | Gil et al. | |
| 10,888,479 B1 | 1/2021 | Gershon et al. | |
| 10,925,561 B2 | 2/2021 | Snow | |
| D912,842 S | 3/2021 | Chou et al. | |
| D920,518 S | 5/2021 | Takahashi | |
| 11,049,626 B1 * | 6/2021 | Ahearn | A61B 90/05 |
| D926,462 S | 8/2021 | Burgon et al. | |
| D936,905 S | 11/2021 | Jefferis et al. | |
| 11,179,287 B1 * | 11/2021 | Mirbahaeddin | A61G 15/10 |
| 11,191,334 B2 | 12/2021 | Aghazadeh et al. | |
| D940,565 S | 1/2022 | Nguyen et al. | |
| D947,679 S | 4/2022 | Hughes et al. | |
| 11,317,986 B1 | 5/2022 | Ahearn | |
| 11,534,256 B2 | 12/2022 | Asamaral | |
| 2003/0234015 A1 * | 12/2003 | Bruce | A61M 15/0016 |
| | | | 128/200.23 |
| 2004/0129860 A1 | 7/2004 | Thibaud | |
| 2004/0177447 A1 | 9/2004 | Love | |
| 2004/0255937 A1 | 12/2004 | Sun | |
| 2005/0011035 A1 | 1/2005 | Rukavina et al. | |
| 2005/0085686 A1 | 4/2005 | Yuen | |
| 2006/0034423 A1 | 2/2006 | Pensel et al. | |
| 2006/0148397 A1 | 7/2006 | Schultz et al. | |
| 2006/0247487 A1 | 11/2006 | Arts et al. | |
| 2007/0125224 A1 | 6/2007 | Thomas | |
| 2008/0033328 A1 | 2/2008 | Chang | |
| 2008/0212337 A1 | 9/2008 | Mangiardi | |
| 2008/0223384 A1 | 9/2008 | Zabari | |
| 2009/0088061 A1 | 4/2009 | Le Beau | |
| 2010/0279594 A1 | 11/2010 | Peeler et al. | |
| 2011/0226123 A1 | 9/2011 | Priebe et al. | |
| 2011/0318702 A1 | 12/2011 | Lockwood | |
| 2013/0101953 A1 | 4/2013 | Stone et al. | |
| 2014/0111977 A1 | 4/2014 | Nyberg | |
| 2014/0316455 A1 | 10/2014 | Gnanashanmugam | |
| 2014/0349561 A1 | 11/2014 | Reiss et al. | |
| 2015/0025300 A1 | 1/2015 | Hill et al. | |
| 2016/0074268 A1 | 3/2016 | Breegi et al. | |
| 2016/0249810 A1 | 9/2016 | Darty et al. | |
| 2016/0353055 A1 | 12/2016 | Popescu et al. | |
| 2017/0208878 A1 | 7/2017 | Kakinuma | |
| 2018/0023799 A1 | 1/2018 | Lumaye et al. | |
| 2018/0163978 A1 | 6/2018 | Ziegler et al. | |
| 2018/0236614 A1 | 8/2018 | Holmes | |
| 2018/0326170 A1 * | 11/2018 | Kamradt | A61M 16/0427 |
| 2019/0105740 A1 | 4/2019 | Vanier | |
| 2019/0330874 A1 | 10/2019 | Pescovitz | |
| 2019/0388290 A1 | 12/2019 | Comunale | |
| 2020/0000541 A1 | 1/2020 | Clemens | |
| 2020/0004676 A1 | 1/2020 | Kubota | |
| 2020/0016774 A1 | 1/2020 | Keen | |
| 2021/0290793 A1 | 9/2021 | Tung | |
| 2021/0330419 A1 * | 10/2021 | Danner | A61G 10/005 |
| 2021/0346564 A1 | 11/2021 | Jetter | |
| 2021/0353380 A1 | 11/2021 | Sellars et al. | |
| 2021/0353469 A1 | 11/2021 | Orrington, II | |
| 2021/0353481 A1 * | 11/2021 | Susec | A61G 10/005 |
| 2022/0053868 A1 * | 2/2022 | Baker | A41D 13/1107 |
| 2022/0072251 A1 * | 3/2022 | Brady | A61M 16/049 |
| 2022/0084199 A1 | 3/2022 | Lee et al. | |
| 2022/0142269 A1 | 5/2022 | Orrington, II et al. | |
| 2022/0226589 A1 * | 7/2022 | Brady | A61M 16/0093 |
| 2022/0257887 A1 * | 8/2022 | Brady | A61B 1/00154 |

FOREIGN PATENT DOCUMENTS

| | | |
|---|---|---|
| CN | 106581867 | 4/2017 |
| CN | 210472180 | 5/2020 |
| EP | 0463282 A1 | 1/1992 |
| EP | 0788776 A1 | 8/1997 |
| EP | 3895653 | 10/2021 |
| EP | 4093317 A4 | 2/2024 |
| EP | 4142643 A4 | 7/2024 |
| IN | 427 | 4/2010 |
| JP | H0549688 A | 3/1993 |
| JP | H06038933 | 5/1994 |
| JP | H08033659 | 2/1996 |
| JP | 2002303436 A | 10/2002 |
| JP | 2007130333 | 5/2007 |
| JP | 2015037475 A | 2/2015 |
| JP | 2016086839 A | 5/2016 |
| JP | 1683418 S | 4/2021 |
| KR | 20150033913 | 4/2014 |
| RU | 80336 U1 | 2/2009 |
| RU | 2008138178 U | 2/2009 |
| WO | WO2000045768 A1 | 8/2000 |
| WO | 2018117804 A1 | 6/2018 |
| WO | WO 2021236241 A1 | 11/2021 |
| WO | WO 2021236245 A1 | 11/2021 |

OTHER PUBLICATIONS

Laura Raskin, Architects, Engineers, and Physicians Develop COVID-19 Patient Isolation Hood, Architectural Record, Apr. 14, 2020, pp. 3-4, ePublishing, Chicago, Illinois, U.S.

Teju Hari Krishna, Researchers design ventilation hoods for hospital beds to help contain COVID-19 spread, Apr. 9, 2020, pp. 1-2, The University of Melbourne, Melbourne, Australia.

Ergonomic Products, Safe-T-Shield , accessed Dec. 6, 2023, published at least as early as Oct. 2, 2020, online at https://ergonomic-products.com/safe-t-shield.

Unicore Dental, External Oral Suction V105, website, accessed Dec. 6, 2023, published at least as early as Oct. 2, 2020, online at https://unicoredental.com.

Dentistry biggest problem has been solved!! AirguardTM, Airguard, Youtube, [Post date: Feb. 24, 2021], [Site seen May 26, 2022], Seen at URL: https://www.youtube.com/watch?v=ARYY-09G.

(56) References Cited

OTHER PUBLICATIONS

Dental Face Shield, Classical Designs, [Post Date unknown], [Site seen May 26, 2022], Seen at URL: https: /glassicaldesigns.com/product/dental-face-shield/ (Year: 2022).

By Anahad O'connor; Really? Flu is Spread Primarily Through Close Contact; published Feb. 11, 2013; The New York Times (Year: 2013).

Airguard LT. Airguard, [Post date: Feb. 15, 2021], [Site seen May 26, 2022], Seen at URL: https://mobile.twitter.com/AirGuardHealth/status/1361314680480927750?cxt=HHwWjMC42aif.

* cited by examiner

PROTECTIVE APPARATUSES FOR MINIMIZING RISK OF TRANSMISSION OF INFECTION AND ASSOCIATED SYSTEMS AND METHODS

FIELD OF THE INVENTION

The present disclosure relates to a protective apparatus for minimizing the risk of transmission of the COVID-19 virus and/or other sources of infection in environments where there is a high risk of transmission due to individuals being in close physical proximity to one another. More particularly, this disclosure relates to a protective apparatus comprising a substantially transparent shield component and a receiving component. Said apparatus may be installable to a substantially cylindrical object such as a vacuum hose or other suctioning device. Said apparatus may be installable to an articulating mechanical arm. This disclosure further relates to methods for minimizing the risk of transmission of an infectious disease comprising installing protective apparatuses enabled by this disclosure to a substantially cylindrical suctioning device or to an articulating mechanical arm, and positioning the suctioning device, or manipulating the mechanical arm, so that the substantially transparent shield component of the protective apparatus is located between the head region of an individual, such as a patient occupying a chair such as a dental chair, and the head region of a healthcare worker treating said patient for example. Such positioning of the substantially transparent shield component is intended, without limitation, to substantially prevent droplets that may emanate from the mouth or nose of such an individual from projecting onto a dentist or other healthcare worker treating said patient in such a manner so as to present a risk of transmission of infection.

BACKGROUND

COVID-19 is an infectious disease caused by severe acute respiratory syndrome coronavirus 2 (SARS-CoV-2). The first cases of COVID-19 were reported in December, 2019, in Wuhan, China. Since that time, the virus has spread throughout the world, resulting in a global pandemic. As of the time of this application filing, more than 48.6 million patients are known to have been diagnosed with COVID-19 across more than 213 countries and territories. As of the date of this disclosure, there have been more than 1.2 million reported deaths due to COVID-19.

SARS-CoV-2 may be transmitted via droplet contact (e.g., coughing and sneezing); direct physical contact; indirect physical contact (e.g., touching a contaminated surface); and airborne transmission. The primary way through which COVID-19 is transmitted, however, is through small droplets produced by coughing, sneezing, and talking, where individuals are in close physical proximity to one another. COVID-19 may be transmitted by persons infected with the virus who have not exhibited any symptoms. Future effects of COVID-19 remain in question, as no known solution exists to mitigate or eliminate these undesirable conditions conducive to ongoing transmission.

Close physical proximity between people increases the risk of transmitting COVID-19 because COVID-19 may be transmitted via at least droplet contact (e.g., coughing and sneezing); direct physical contact; indirect physical contact (e.g., touching a contaminated surface); and airborne transmission. Social distancing, also referred to as physical distancing, is one of the primary tactics that have been utilized throughout the world to attempt to contain the spread of the COVID-19 virus. Social distancing comprises maintaining certain minimum physical distances between individuals and reducing the number of times that individuals come into close physical contact with one another. However, not all activities permit of maintaining sufficient minimum physical distances. For example, many healthcare workers must come within close proximity to their patients in order to perform their duties. Where close physical proximity between people cannot be avoided, there exists a need for a system that is effective in reducing the risk of transmitting COVID-19.

Particles are classified based on size. Coarse particles are 2.5 to 10 microns. Fine particles are less than 2.5 microns. Ultrafine particles are those less than 0.1 microns in size. A human nose generally filters particles larger than 10 microns. If a particle is less than 10 microns, it can enter the respiratory system. If a particle is less than 2.5 microns, it can enter the alveoli. An ultrafine particle can enter the bloodstream and target organs. COVID-19 exists as ultrafine particles.

Current research suggests that most respiratory transmission of COVID-19 occurs through large respiratory droplets. Such large droplets typically fall to the ground after travelling approximately six feet at the most. Activity such as coughing and sneezing, however, can aerosolize the droplets so that they can travel further thereby increasing the risk of transmission (i.e., where the droplets are carrying COVID-19). When aerosolized, COVID-19 can travel up to approximately 20 feet and will remain suspended in the air longer than when not aerosolized. In addition to coughing and sneezing, respiratory droplets are routinely aerosolized in the practice of dentistry.

Dentists who utilize aerosolization in their practice, and therefore their staff as well, are at a high risk of becoming infected with COVID-19. Such dentists' patients are likewise at high risk of becoming infected from the dentist, as well as their dental assistants in the immediate area when being treated. Most such risk results from splatter and droplet transmission to the mid-face of the dentist and assistant and to the nasal area of the patient.

SUMMARY

Protective apparatuses enabled by this disclosure advantageously solve deficiencies known in the current state of the art. In one embodiment enabled by this disclosure, a protective apparatus is enabled that advantageously enhances effectiveness in reducing the risk of transmitting COVID-19 or other infectious disease by mitigating direct, indirect, and/or other contact between individuals. In one embodiment enabled by this disclosure, protective apparatuses for minimizing risk of transmission of an infectious disease may comprise a substantially transparent shield component and a receiving component. The receiving component contemplated by this disclosure may comprise a first aperture comprising a series of flanges through which a substantially cylindrical suctioning device may be inserted. Said suctioning component may exert a negative air pressure to remove airborne pathogens and other infectious agents attached to the downward-facing surface of the substantially transparent shield component and from the space below said surface but above the head region of an individual occupying a chair or other object positioned underneath said shield component. According to an embodiment enabled by this disclosure, securing means supplemental to the first aperture and associated flanges may provide additional stability for, and may help hold substantially in place, said suctioning device upon insertion thereof through said first aperture. According to an embodiment enabled by this disclosure, the substantially transparent shield component may comprise a substantially impermeable, light-weight, plastic between approximately 2 millimeters and approximately 5 millimeters in thickness, without limitation.

Protective apparatuses enabled by this disclosure, alone and as part of a system further comprising a substantially cylindrical suctioning device or articulating mechanical arm, may be employed in a healthcare environment such as a dentist's office to mitigate the risk of transmission of COVID-19 or another infectious disease from patient to dentist or dental assistant, and from dentist or dental assistant to patient. The foregoing example of how protective apparatuses according to the present disclosure may be used is not intended to be limiting but rather is intended to further illustrate the utility of the protective apparatuses contemplated herein. Such methods of use may comprise, by way of illustration, installing a protective apparatus enabled by this disclosure upon a substantially cylindrical vacuum hose, or operatively attaching such a protective apparatus to an articulating mechanical arm, and positioning the resulting system so that the substantially transparent shield component of the protective apparatus is located between the head region of, for example, a patient occupying a chair such as a dental chair and the head region of a healthcare worker treating said patient.

DETAILED DESCRIPTION

Figure 1:
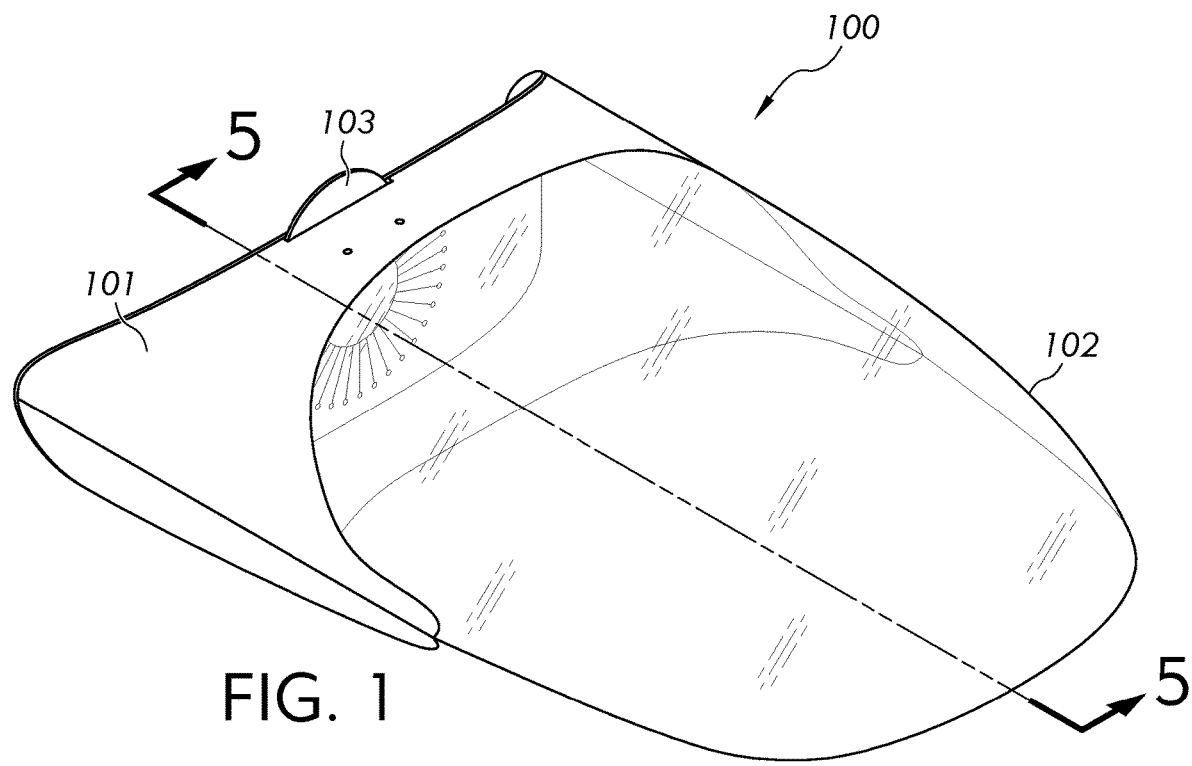
FIG. 1 is a top perspective view of a protective apparatus of the present disclosure.

The following disclosure is provided to describe various embodiments of a protective apparatus intended to minimize the risk of transmission of COVID-19 and other viruses and infectious agents that may be transmitted between individuals in close physical proximity and/or who may interact with common surfaces or objects, as well as related systems and methods involving said protective apparatuses. The protective apparatuses of the present disclosure may be installable to a vacuum hose or other substantially cylindrical suctioning device. The protective apparatuses of the present disclosure may, alternatively, be operatively attached to an articulating mechanical arm (i.e., a mechanical arm capable of articulating).

Skilled artisans will appreciate additional embodiments and uses of the protective apparatuses and associated systems and methods that extend beyond the examples of this disclosure. Terms included by any claim are to be interpreted as defined within this disclosure were such terms are so defined. Singular forms should be read to contemplate and disclose plural alternatives. Similarly, plural forms should be read to contemplate and disclose singular alternatives. Conjunctions should be read as inclusive except where stated otherwise.

Expressions such as "at least one of A, B, and C" should be read to permit any of A, B, or C singularly or in combination with the remaining elements. Additionally, such groups may include multiple instances of one or more elements in that group, which may be included with other elements of the group. All numbers, measurements, and values are given as approximations unless expressly stated otherwise.

Terms and expressions used throughout this disclosure are to be interpreted broadly. Terms are intended to be understood respective to the definitions provided by this specification. Technical dictionaries and common meanings understood within the applicable art are intended to supplement these definitions. In instances where no suitable definition can be determined from the specification or technical dictionaries, such terms should be understood according to their plain and common meaning. However, any definitions provided by the specification will govern above all other sources.

Those of skill in the art will appreciate that alternative labeling of the apparatuses may be provided, which is consistent with the scope and spirit of this disclosure. Skilled readers should not view the inclusion of any alternative labels as limiting in any way.

Various objects, features, aspects, and advantages described by this disclosure will become more apparent from the following detailed description, along with the accompanying drawings.

For the purpose of clearly describing the components and features discussed throughout this disclosure, some frequently used terms will now be defined, without limitation. The term "COVID-19," as it is used throughout this disclosure, is defined as an infectious disease caused by severe acute respiratory syndrome coronavirus 2 (SARS-CoV-2). The term "aerosol," as it is used throughout this disclosure, is defined as a suspension of fine solid particles or liquid droplets in air or another gas. The term "individual," as it is used throughout this disclosure, should not be interpreted in any limiting manner, should be interpreted broadly, and should be interpreted, without limitation, as synonymous with "subject." The term "hole," as it is used throughout this disclosure, is intended to refer exclusively to the series of holes appearing one each at the base of each flange along the interior of the "first aperture" as such term is used herein. The term "hole" is used in this way to maintain clarity relative to the "first aperture," "second aperture," and "third aperture," described herein. The term "head region," as it is used throughout this disclosure, is defined as the area spanning from approximately an individual's neck to approximately the top of the individual's head.

Various aspects of the disclosure will now be described in detail, without limitation. In the following disclosure, protective apparatuses for minimizing risk, such as due to individuals' close physical proximity to one another, of transmission of COVID-19 and other viruses and infectious agents will be discussed.

Protective apparatuses of the present disclosure may be used in a number of different environments. Without limitation, protective apparatuses of the present disclosure may be installed upon a vacuum hose in a dentist's office. In such embodiment the protective apparatus may shield the dentist or other involved healthcare worker from the risk of transmission of infectious agents to them through aerosols emanating from a patient (whom the healthcare worker is treating) occupying an object such as a chair (and likewise may mitigate the risk of transmission of infectious agents to the patient as well). Such risk mitigation may be achieved, without limitation, by positioning a substantially transparent shield component of the protective apparatus between the head region of the patient and the head region of a healthcare worker treating the patient. This may be accomplished, without limitation, by installing the protective apparatus to a vacuum hose or other substantially cylindrical suctioning device and positioning the suctioning device so that the substantially transparent shield component is located between the head region of the patient and the head region of a healthcare worker treating the patient. Similarly, protective apparatuses enabled by this disclosure may be operatively attached to an articulating mechanical arm and the articulating arm may be manipulated so as to position the substantially transparent shield component of a protective apparatus enabled by this disclosure between the head region of a patient and the head region of a healthcare worker treating said patient so as to mitigate the risk of, for example, aerosolized droplets potentially containing infectious agents from projecting onto the healthcare worker from the patient or from projecting from the healthcare worker onto the patient.

Referring now to FIGS. 1-3 and 5, apparatuses enabled by this disclosure 100 will now be discussed in more detail. Apparatuses enabled by this disclosure may comprise, at one end, a receiving component 101 comprising a first aperture 200, 300. Said first aperture may be structured so as to accommodate an object having a substantially cylindrical shape including, without limitation, a vacuum hose 500. The first aperture may be sized so as to accommodate substantially cylindrical objects of varying diameters, including, without limitation, such objects having outside diameters of between approximately 2 inches and approximately 6 inches, more preferably objects having outside diameters of between approximately 3 inches and approximately 5 inches. The latter such sizing is particularly advantageous, without limitation, in that it renders such protective apparatuses substantially universal with regard to the breadth of suctioning devices to which they may be installed.

The receiving component 101 may be comprised of any number of light-weight materials including, without limitation, cardboard.

Figure 2:
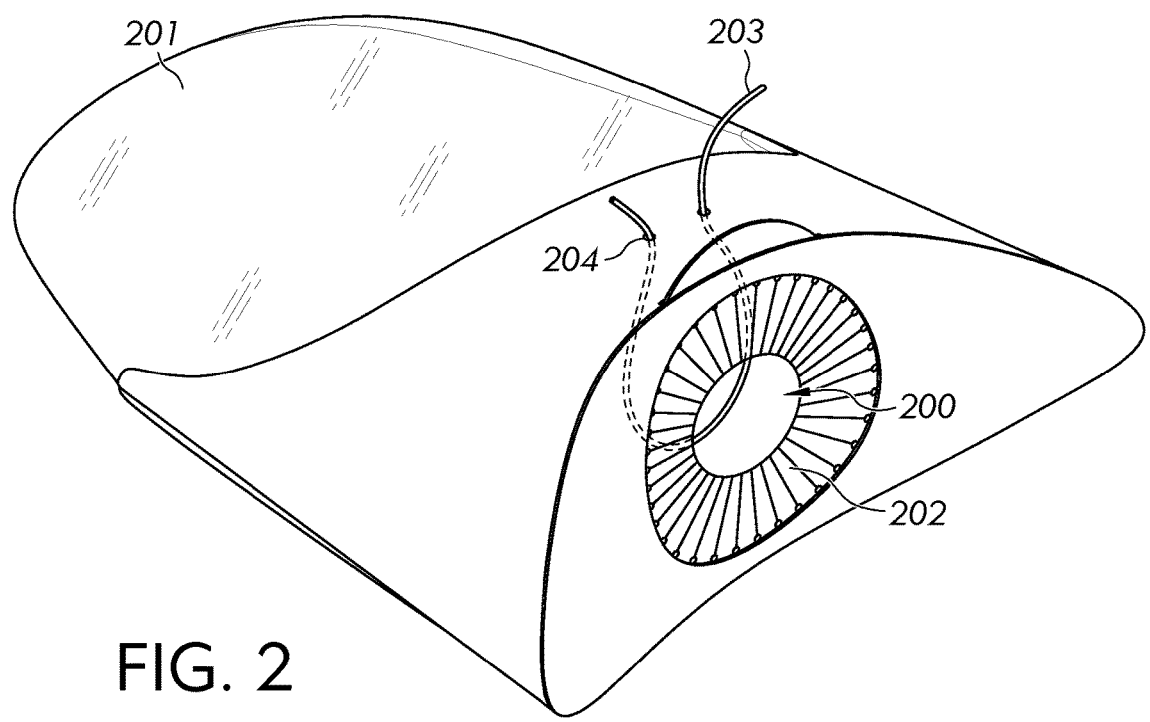
FIG. 2 is a top perspective view of a protective apparatus of the present disclosure.
Figure 3:
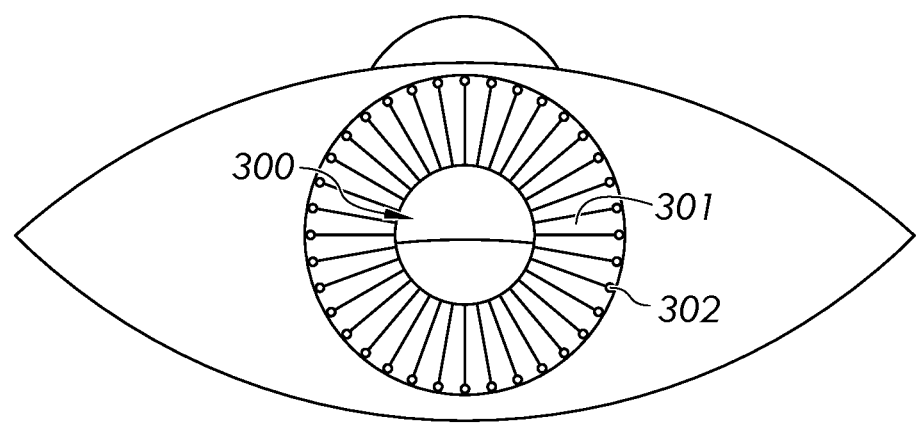
FIG. 3 is a rear perspective view of a protective apparatus of the present disclosure.

Referring now to FIGS. 2 and 3, the first aperture 200, 300 will now be discussed in greater detail. First apertures of the present disclosure may be substantially circular in shape. Such first apertures may comprise a series of flanges 202, 301 extending inward toward a central point inside the first aperture. The first aperture may comprise between approximately 15 and approximately 35 flanges, preferably between approximately 20 and approximately 30 flanges.

The first aperture of the receiving component, including the associated flanges, are intended to accommodate placement of a substantially cylindrical object through the first aperture and flanges. The friction generated by insertion of a substantially cylindrical object having an outer diameter of between approximately two inches and approximately six inches, preferably between approximately three inches and approximately five inches, serves as means for holding the substantially cylindrical object securely in place.

Each flange may also comprise a round hole 302 located approximately near the end of the flange located approximately at the outer perimeter of the first aperture. These round holes help prevent tearing at or near the base of the flanges by decreasing the physical stress associated with insertion of an object through the first aperture and flanges. The first aperture, including the associated flanges, may be located at an approximately central location on the receiving component so as to contribute to substantially stable positioning of the receiving component around a substantially cylindrical object 500 upon insertion of such object through the first aperture.

The portion of the receiving component comprising the first aperture and associated flanges as described herein may further include a tab 103 that protrudes from said portion. Such protruding tab facilitates handling of the protective apparatuses enabled by this disclosure.

A string 203 or similar restraining means such as a rope, cord, zip-tie, or thread may be used to further secure the substantially cylindrical object and hold it substantially stationary upon insertion thereof through the first aperture and flanges. According to such an embodiment, the receiving component may further comprise, on its outer surface, second and third apertures 204 through which the string or similar restraining means may be inserted as supplemental securing means for holding the substantially cylindrical object substantially stationary. According to such an embodiment, these two apertures may be approximately 0.13 and 0.38 inches in diameter each.

As depicted in FIG. 2, a first and second end of the string or other restraining means may be pulled through the second and third apertures, respectively, so that said string or other restraining means extends to the interior of the receiving component through which the substantially cylindrical object will extend upon insertion. By so positioning the string or other restraining means, said string or other restraining means may be wrapped around a suctioning device or other object that has been inserted through the first aperture, thus providing for additional stability for said object. These second and third apertures may be positioned so that they are between approximately one inch apart and approximately two inches apart, without limitation.

Figure 4:
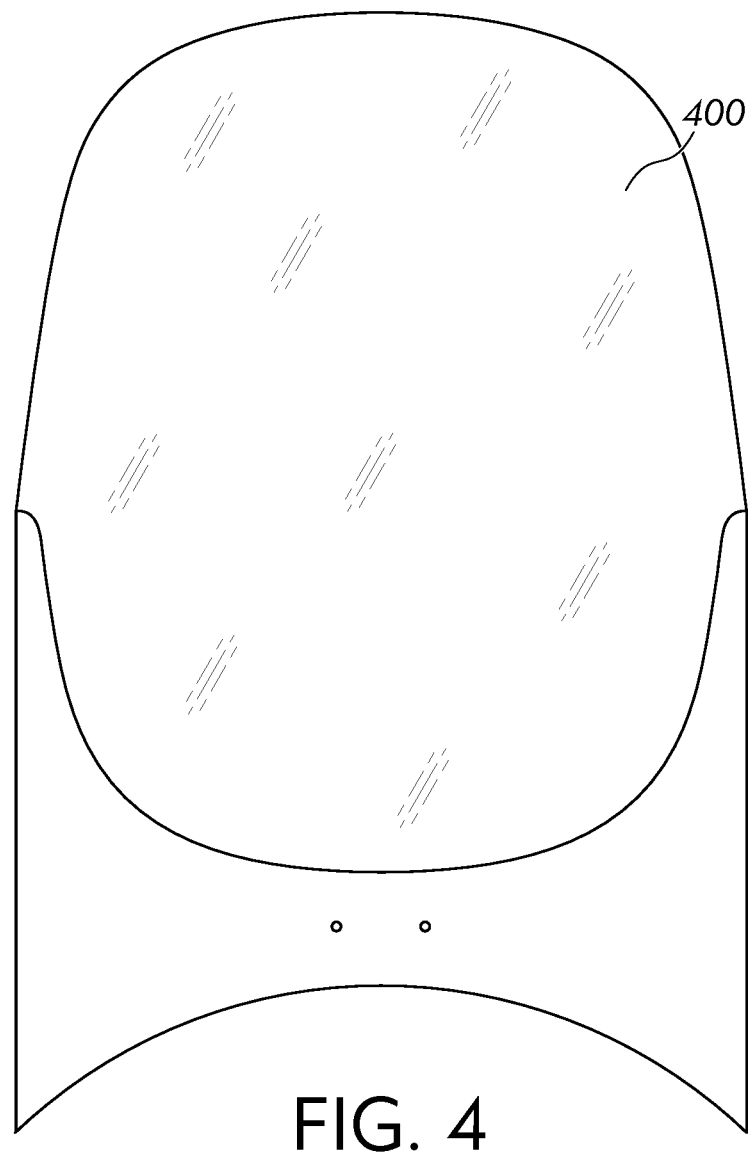
FIG. 4 is a top plan view of a protective apparatus of the present disclosure.
Figure 5:
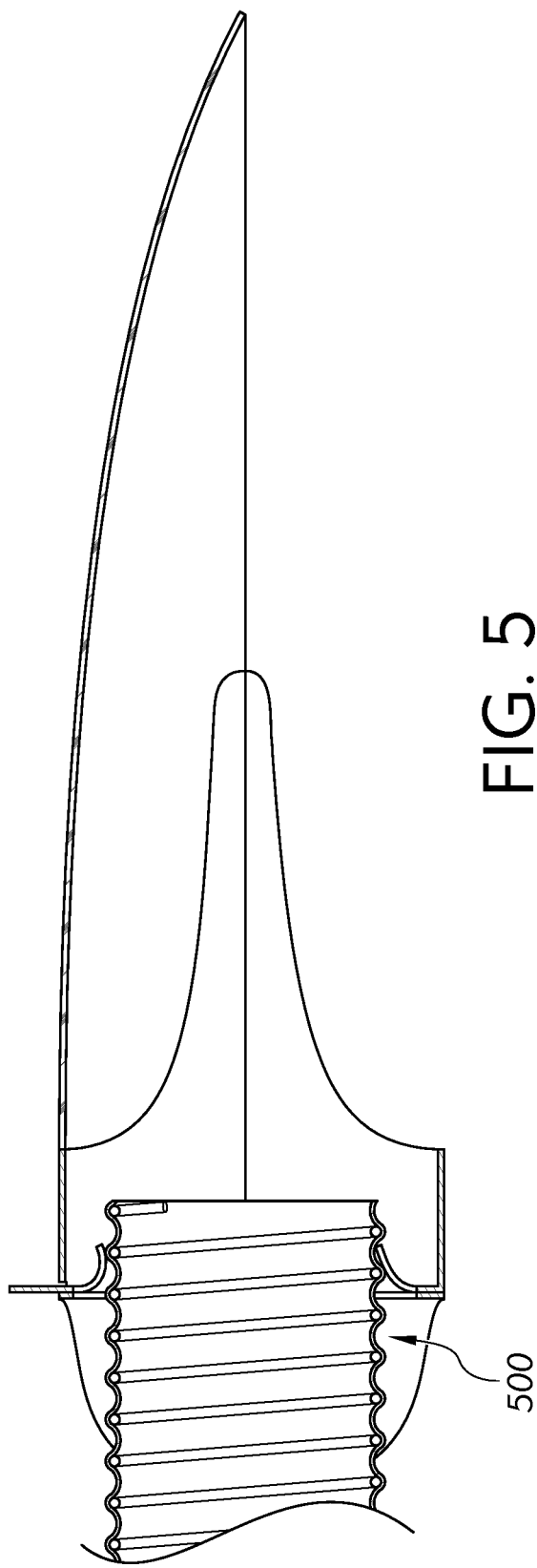
FIG. 5 is a side elevation view of a protective apparatus of the present disclosure installed upon a substantially cylindrical suctioning device.

Referring now to FIGS. 1, 2, and 4, the substantially transparent shield component, 102, 201, 400 will be discussed in greater detail. The substantially transparent shield component may be comprised of any number of materials suitable for serving as a substantially impermeable protective barrier. The substantially transparent shield component may be comprised of any solid material that is both substantially impermeable and substantially transparent such as, without limitation, certain types of plastic or clear glass. The plastics that may be suitable for use in making the shield component may comprise, without limitation, polyethylene terephthalate glycol (or PETG), polymethyl methacrylate, cellulose acetate butyrate, or polycarbonate.

Preferably, the shield component may be comprised of a light-weight material to facilitate easy handling thereof. In one embodiment, the shield component may be constructed using materials that are not toxic to human beings. Said material may be approximately 1.5 millimeters to approximately 6 millimeters in thickness, without limitation. More preferably, said material may be approximately 2 millimeters to approximately 5 millimeters in thickness, without limitation.

The substantially transparent shield component of the protective apparatuses enabled by this disclosure may be between approximately six inches and approximately 22 inches in length, without limitation. More preferably, the substantially transparent shield component may be between approximately nine inches and approximately 18 inches in length, without limitation.

The substantially transparent shield component of the protective apparatuses of the present disclosure may have any number of contours. The substantially transparent shield component may slope upward on the left-hand side and the right-hand side thereby comprising a concave shape. The substantially transparent shield component may comprise protrusions to accommodate the curvature of an individual's face.

The substantially transparent shield component of the protective apparatuses enabled by the present disclosure may be detachable from the receiving component and may be replaceable. Alternatively, the substantially shield component and the receiving component may comprise a single unit.

By way of illustration only, protective apparatuses enabled by the present disclosure may be constructed using flat stock material that may comprise glue or similar adhesive on one side. Such material may be folded into a three-dimensional structure that is self-supporting. Protective apparatus enabled by the present disclosure may be supplied in a knock-down kit. Such flat stock material and knock-down kit assembly helps to reduce manufacturing costs, reduce shipping costs, reduce the required storage space, and increase the ease of disposal.

Protective apparatus enabled by the present disclosure may be installable to a vacuum hose or other suctioning device substantially cylindrical in shape. In such embodiment, said suctioning device may produce a negative air pressure thereby removing air from the space immediately underneath the substantially transparent shield component. In such embodiment, the negative air pressure generated by the suctioning device may remove and facilitate removal of infectious agents present immediately underneath the substantially transparent shield component and/or attached to the downward-facing surface of the substantially transparent shield component.

In another embodiment, protective apparatuses enabled by the present disclosure may be operatively attached to an articulating mechanical arm. Said articulating arm may be located and manipulated so that the substantially transparent shield component of the protective apparatus is positioned overtop of the head region of an individual so as to minimize the risk of droplets of saliva potentially containing infectious agents, and/or of airborne infectious agents, projecting from the individual onto others in the vicinity of the individual, and from reaching the individual if exuded from others in the individual's vicinity.

Systems for mitigating the risk of transmission of an infectious disease as contemplated by this disclosure may, without limitation, comprise protective apparatuses as described herein installed upon a suctioning device comprising a substantially cylindrical vacuum hose. Those of skill in the art will recognize that additional components may, optionally, be added to said system. Such additional components may comprise, without limitation, a chamber component comprising means for disinfecting air entering the suctioning device discussed herein. Such disinfecting means may comprise, without limitation diodes emitting ultraviolet light.

In another embodiment, systems enabled by this disclosure may comprise a protective apparatus enabled by this disclosure operatively attached to an articulating mechanical arm. Such a system may, optionally, further comprise a suctioning device for removing infectious agents from the downward-facing surface of the substantially transparent shield component of the protective apparatus and from the area underneath said downward-facing surface but above an individual over whom the substantially transparent shield component has been positioned.

Protective apparatuses enabled by the present disclosure, as well as associated systems as described herein, may be used, without limitation, in a dentist's office to minimize the risk of transmission of an infectious disease between, for example, patient and dentist, or between patient and dental assistant or other individual present near the work area where the dental patient is being treated. Those of skill in the art will readily recognize that protective apparatuses and associated systems enabled by the present disclosure may be used to mitigate the risk of transmission of an infectious disease between patient and healthcare worker in clinical settings other than dentists' offices as well such as, for example, in a hospital setting or any other clinical setting where patient and healthcare worker are in close physical proximity to one another.

The protective apparatuses and associated systems contemplated by this disclosure may be used in connection with methods for mitigating the risk of transmission of an infectious disease by mitigating the risk of potential exposure to droplets comprising infectious agents and/or to airborne infectious agents. Such methods, may comprise, without limitation, installing the receiving component of the protective apparatuses described herein to a substantially cylindrical suctioning device; locating the suctioning device such that the substantially transparent shield component of the protective apparatus extending therefrom is positioned between the head region of a healthcare worker and the head region of a patient whom the healthcare worker is treating; and actuating the suctioning device so that it exerts a negative air pressure toward a downward-facing surface of the substantially transparent shield component and the space below said surface. Those of skill in the art will readily appreciate the sorts of actuating means, such as, without limitation, physically manipulable control components, that are commonly incorporated into suctioning devices such as suctioning devices commonly employed in a dentist's offices, without limitation.

Alternatively, methods enabled by the present disclosure may comprise protective apparatuses as described herein operatively attached to an articulating mechanical arm, with and without an associated suctioning device. According to such methods, the protective apparatus may be attached to the mechanical arm; and the mechanical arm may be manipulated such that the substantially transparent shield component of the protective apparatus extending therefrom is positioned between, for example, the head region of a healthcare worker and the head region of a patient whom the healthcare worker is treating. Such methods may further comprise locating a suctioning device such that said device may remove infectious agents present immediately underneath the substantially transparent shield component and/or attached to the downward-facing surface of the substantially transparent shield component.

While various aspects of the protective apparatuses enabled by this disclosure, as well as associated systems and methods for mitigating the risk of transmission of an infectious disease, have been described above, the description of this disclosure is intended to illustrate and not limit the scope of the invention. The invention is defined by the scope of the claims and not the illustrations and examples provided in the above disclosure. Skilled artisans will appreciate additional aspects of the protective apparatuses, and the associated systems and methods, enabled by this disclosure, which may be realized in alternative embodiments, after having the benefit of the above disclosure. Other aspects, advantages, embodiments, and modifications are within the scope of the claims.

What is claimed is:

1. A protective apparatus comprising:
   a receiving component comprising a first aperture comprising cardboard flanges located within the first aperture and extending inwardly towards a central point within the aperture, wherein each flange comprises a round hole located near the end of the flange located at the outer perimeter of the first aperture; and
   a transparent shield component comprised of an impermeable material.

2. The protective apparatus of claim 1, wherein each hole is located near the end of each of the flanges to decrease physical stress associated with inserting a suctioning device through at least part of the aperture.

3. The protective apparatus of claim 1, wherein the transparent shield component is between 2 millimeters in thickness and 5 millimeters in thickness.

4. The protective apparatus of claim 1, wherein said first aperture has a diameter of between two inches and five inches.

5. The protective apparatus of claim 2, wherein the receiving component further comprises a second aperture and a third aperture spaced between one inch and two inches apart from one another, wherein said second aperture and said third aperture open on one side to an exterior of the protective apparatus and open on the opposite side to an interior of the protective apparatus above the first aperture, and wherein the protective apparatus further comprises a string extending through each of the second aperture and the third aperture.

6. A method for mitigating the risk of transmission of an infectious disease, said method comprising:
   acquiring the protective apparatus of claim 1;
   attaching a suctioning device comprising a substantially cylindrical hose to the first aperture;
   locating the transparent shield component between a head region of a patient and a head region of a healthcare worker treating said patient; and
   actuating the suctioning device so that it exerts a negative air pressure toward a downward-facing surface of the transparent shield component and the space below said surface.

7. The method of claim 6, further comprising inserting said substantially cylindrical hose through the first aperture generating friction between the substantially cylindrical hose and the flanges to hold the substantially cylindrical hose in place within the first aperture.

8. The method of claim 6 wherein the protective apparatus further comprises a mechanical arm, the method further comprising:
   articulating the mechanical arm to position the transparent shield component between users to mitigate the risk of aerosolized droplets potentially containing infectious agents projecting from one or more of the users.

9. The method of claim 6 wherein the receiving component further comprises a second aperture and a third aperture spaced between one inch and two inches apart from one another, wherein said second aperture and said third aperture open on one side to the exterior of the protective apparatus and open on the opposite side to the interior of the protective apparatus above the first aperture, and wherein the protective apparatus further comprises a string extending through each of the second aperture and the third aperture.

10. The method of claim 9, wherein the impermeable material comprises polyethylene terephthalate glycol.

11. A system for mitigating risk of transmission of an infectious disease, said system comprising:
    a protective apparatus comprising:
      a receiving component; and
      a transparent shield component;
      wherein said receiving component comprises a first aperture comprising cardboard flanges located within the first aperture each extending radially inwardly towards a central point within the first aperture, wherein each flange comprises a round hole located near the end of the flange located at the outer perimeter of the first aperture; and
      wherein the transparent shield component is comprised of an impermeable material; and
    a suctioning device comprising a substantially cylindrical hose.

12. The system of claim 11, wherein said substantially cylindrical hose passes through the first aperture generating friction between at least part of the suctioning device and the flanges for holding the substantially cylindrical hose in place within the first aperture.

13. The system of claim 11, wherein the transparent shield component is 2 millimeters in thickness.

14. The system of claim 11 wherein the impermeable material comprises polyethylene terephthalate glycol.

15. The system of claim 11, wherein the receiving component further comprises a second aperture and a third aperture spaced between one inch and two inches apart from one another, wherein said second aperture and said third aperture are each open on one side to an exterior of the protective apparatus and open on an opposite side to the interior of the protective apparatus above the first aperture, and wherein the protective apparatus further comprises a string extending through each of the second aperture and the third aperture.

16. A system for mitigating risk of transmission of an infectious disease, said system comprising:
    a protective apparatus comprising:
      a receiving component comprising a first aperture comprising cardboard flanges located within the first aperture and extending inwardly towards a central point within the first aperture, wherein each flange comprises a round hole located near the end of the flange located at the outer perimeter of the first aperture;
      a transparent shield component comprised of an impermeable material extending from the receiving component; and
    a mechanical arm capable of articulating so as to position the transparent shield component to mitigate the risk of aerosolized droplets potentially containing infectious agents from projecting between users.

17. A method for mitigating the risk of transmission of an infectious disease, said method comprising:
    providing the system of claim 16;
    attaching said protective apparatus to said mechanical arm, and
    locating the transparent shield component between a head region of a patient and a head region of a healthcare worker treating said patient.

* * * * *